United States Patent
Marishak, Jr.

(10) Patent No.: US 7,106,215 B2
(45) Date of Patent: Sep. 12, 2006

(54) DEVICE FOR MONITORING THE INTEGRITY OF SPACECRAFT THERMAL PROTECTION TILES

(76) Inventor: Frank Ted Marishak, Jr., 6423 White House Rd., Moneta, VA (US) 24121

( * ) Notice: Subject to any disclaimer, the term of this patent is extended or adjusted under 35 U.S.C. 154(b) by 288 days.

(21) Appl. No.: 10/775,392

(22) Filed: Feb. 10, 2004

(65) Prior Publication Data

US 2005/0200493 A1    Sep. 15, 2005

(51) Int. Cl.
*G08B 21/00*    (2006.01)

(52) U.S. Cl. ............... 340/945; 340/652; 324/526

(58) Field of Classification Search ............ 340/945
See application file for complete search history.

(56) References Cited

U.S. PATENT DOCUMENTS

| | | | |
|---|---|---|---|
| 3,383,863 A | | 5/1968 | Berry |
| 3,477,019 A | | 11/1969 | Hartmann |
| 3,509,942 A | * | 5/1970 | Lindberg .................... 340/945 |
| 3,596,269 A | * | 7/1971 | Laska ......................... 340/518 |
| 3,803,485 A | * | 4/1974 | Crites et al. ................ 324/693 |
| 3,956,731 A | * | 5/1976 | Lewis, Jr. ................... 340/945 |
| 4,255,974 A | * | 3/1981 | Dufrane et al. ............... 73/776 |
| 4,336,595 A | * | 6/1982 | Adams et al. ................ 702/34 |
| 4,344,591 A | * | 8/1982 | Jackson ................... 244/159.1 |
| 4,503,710 A | | 3/1985 | Oertle et al. |
| 4,524,620 A | * | 6/1985 | Wright et al. ................ 73/587 |
| 4,546,652 A | * | 10/1985 | Virkar et al. ................ 73/776 |
| 4,557,444 A | * | 12/1985 | Jackson et al. .......... 244/159.1 |
| 4,713,275 A | * | 12/1987 | Riccitiello et al. ............ 428/76 |
| 5,195,046 A | * | 3/1993 | Gerardi et al. ............... 702/35 |
| 5,350,138 A | * | 9/1994 | Culbertson et al. ...... 244/159.6 |
| 5,382,909 A | * | 1/1995 | Masia et al. ................ 324/525 |
| 5,425,275 A | * | 6/1995 | Lockshaw .................... 73/775 |
| 5,816,530 A | * | 10/1998 | Grube ........................ 244/1 R |
| 5,928,775 A | * | 7/1999 | DiChiara et al. ......... 428/312.2 |
| 6,172,511 B1 | * | 1/2001 | Nicholls et al. ............. 324/713 |
| 6,289,289 B1 | * | 9/2001 | Zweifel ....................... 340/966 |
| 6,449,565 B1 | * | 9/2002 | Budrow et al. ............... 702/42 |
| 6,806,808 B1 | * | 10/2004 | Watters et al. ........... 340/10.41 |
| 6,889,557 B1 | * | 5/2005 | Richardson et al. .......... 73/809 |

* cited by examiner

*Primary Examiner*—Daniel Wu
*Assistant Examiner*—Eric Blount
(74) *Attorney, Agent, or Firm*—Rodney A. Corl

(57) ABSTRACT

An electrical circuit, attached to the tiles of the space shuttle, provides an indication of tile integrity in real time. Each tile has a resistor attached thereto between parallel conductors, and a series of tiles forms a protected grid series tile section. A computer, in conjunction with an ohm measuring device, continually monitors the tile integrity by comparing the baseline resistance of the protected grid series tile section to a measured value. A substantial difference in resistance between the measured value and the baseline value indicates the location and magnitude of a loss in integrity in the section, and an indication of such is provided to the shuttle crew. The conductors may be formed within the tile or may be attached to the thermally protected side of the tile.

7 Claims, 2 Drawing Sheets

DEVICE FOR MONITORING THE INTEGRITY OF SPACECRAFT THERMAL PROTECTION TILES

BACKGROUND OF THE INVENTION

The U.S. space program has relied on the reusable space transportation system (space shuttle) to do the bulk of its work in carrying cargo and satellites into low earth orbit, as well as for retrieving satellites from orbit and performing maintenance and repairs on them. In general, this system has performed remarkably well, with each shuttle vehicle being reused many times. However, the recent shuttle disaster in 2003, where the shuttle Columbia broke up on reentry into the atmosphere due to a loss of integrity in the thermal protection tiles, brings to light the fallibility of the thermal protection tile system and raises a need for a means to guard against future disasters of this type. To date, there is no means for monitoring the integrity of the thermal tiles on the space shuttle during flight. While it has been attempted to assess the integrity of the tiles visually, by means of cameras or even by direct visual inspection during spacewalks, these methods are not very accurate as the tiles may be loose or cracked and these faults would not be observed visually.

U.S. Pat. No. 3,596,269 utilizes a number of resistance elements connected in parallel to indicate structural fatigue cracking and tearing in aircraft. Resistance elements are in parallel and apparently measure the degree of stress failure by determining the intensity of the resistance. One end of the circuit is grounded, and a complete break in the circuit would render this method useless.

U.S. Pat. No. 3,383,863 detects leaks in retaining pond linings by a grid of wires laid beneath the lining. When water or other fluid leaks from the pond through the lining an electrical circuit is completed between the separated intersecting connectors of the grid. The location of the leak is determined by measuring the resistance between crossing grid members, the leak being in the vicinity of the intersection of least resistance.

U.S. Pat. No. 4,503,710 describes a means for monitoring the integrity of a structure in a fluid tight environment, and measures a change in resistance due to a leak in the environment, which indicates a crack or break in the structure.

U.S. Pat. No. 3,477,019 shows an electrical circuit utilizing resistors to pinpoint the location of ground movement. The resistance is measured and a break in the circuit registers as a change in resistance, the magnitude of the resistance indicating the location of the break.

While the aforementioned patents indicate the use of resistance measuring circuits to detect the loss of integrity in the circuit, none specifically addresses the unique problems encountered in the thermal protection tiles of the space shuttle.

BRIEF SUMMARY OF THE INVENTION

The present invention relates to the phase of flight of the space shuttle known as re-entry into the earth's atmosphere. During this critical phase of flight, the shuttle is subjected to extreme temperatures due to the friction between the shuttle's outer skin and the increasing density of the atmosphere. The shuttle is protected from the effects of the extreme high temperatures by a heat shield consisting of an outer layer of thousands of heat insulating tiles. These tiles are glued, or in other means adhered, to the underlying metal skin of the shuttle, providing an aerodynamic, heat insulating surface. Problems have been encountered with the tile system since its inception. The integrity of the heat shield tiles may be compromised through foreign object damage during the lift-off phase of fight or by space debris encountered after leaving the earth's atmosphere. These tiles are subject to extremes in hot and cold, and have cracked, come loose, and even come off of the shuttle during re-entry. The recent tragic loss of the shuttle Columbia during re-entry into the earth's atmosphere has been blamed on the loss of tiles on the wing, and the resulting thermal destruction of the underlying wing structures. Presently, there is no system on the shuttle that assures the tile integrity after lift-off and prior to the shuttle's critical re-entry phase.

Therefore, it is an object of the present invention to provide a means to monitor the integrity of the heat shield tiles on the space shuttle. To accomplish this object, each tile is provided with an electrically conductive portion of a circuit, having a resistor therein, wherein each tile is connected to an adjacent tile electrically. A row of tiles may be connected together to form a resistance bridge circuit. A loss of integrity in the thermal tiles would cause a break in the circuit, which can be detected by measuring a change in the resistance of the circuit. The location of the loss in the integrity in the tiles is a function of the magnitude of the change in resistance. It is another object of the present invention to provide a method of monitoring the integrity of the heat shield tiles on the space shuttle, and to assess the extent and location of damage to the heat shield tiles in real time. The circuits formed throughout the rows of thermal tiles are all connected to a computer which continually monitors the resistance of each circuit, and signals to the shuttle occupants a loss of tile integrity, as well as the location of the loss in integrity. These objects and others will be fully described with reference to the accompanying drawings and detailed description.

BRIEF DESCRIPTION OF THE DRAWINGS

The invention will be further described in connection with the accompanying drawings, in which.

DETAILED DESCRIPTION

Figure 1:
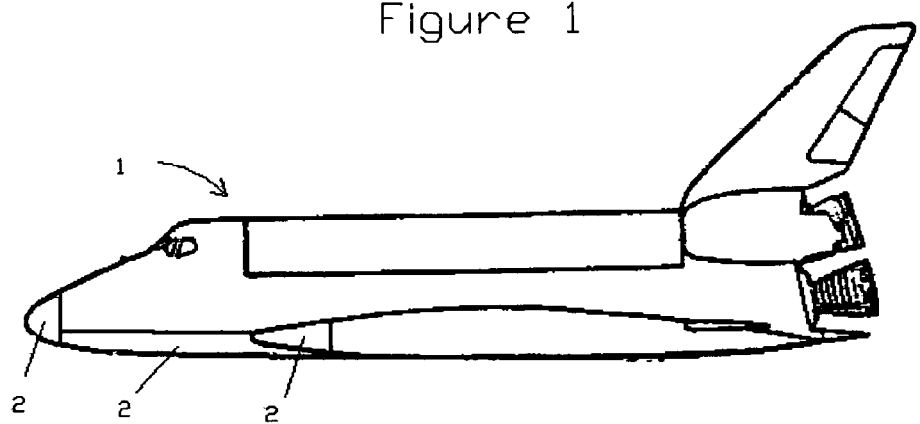
FIG. 1 is a side view of the space shuttle showing tile placement on the wings, body underside, and nose portions.

In FIG. 1, a vehicle known as the Space Transportation System, or space shuttle, is shown. Space shuttle 1 has a thermally protective layer 2, comprised of tiles attached to the areas of the shuttle that are exposed to extremely high temperatures during the phase of flight known as re-entry. These areas are typically the wings, especially the leading edges thereof, the nose portion of the fuselage, and the underside of the fuselage. Currently, the integrity of these tiles is assessed between flights, and there are no means to assess integrity of the tiles before or during the critical re-entry phase of flight.

Figure 2:
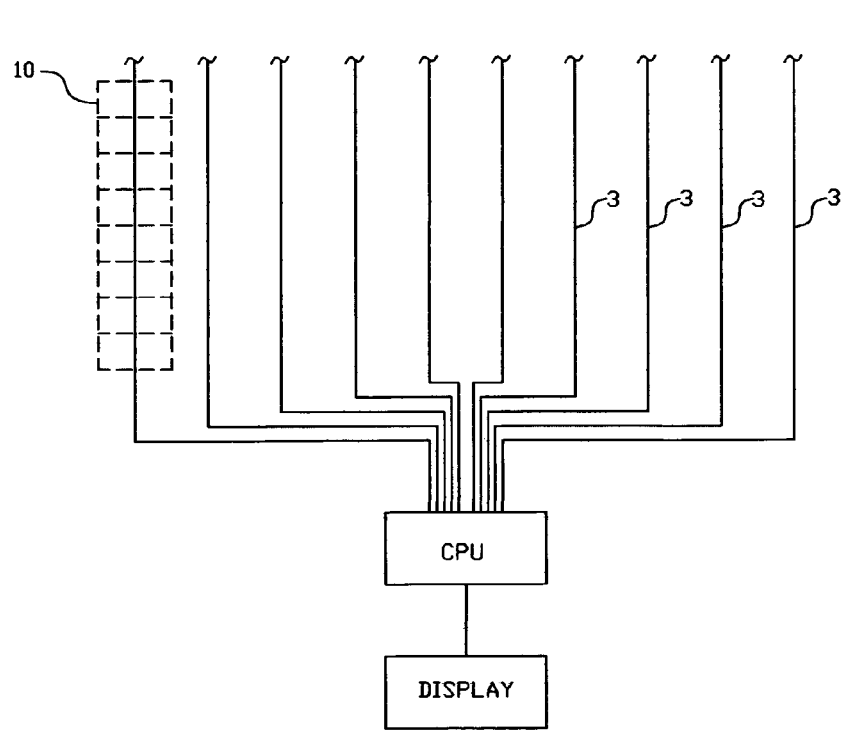
FIG. 2 is an electronic schematic diagram of the present invention.

Referring to FIG. 2, a means is provided to monitor the integrity of the tiles in real time, during flight of the shuttle. Rows of tiles are provided with an electrically conductive circuit 3 which is then in turn connected to a computing device 4 which can monitor the state of the circuits 3 continually, and provide an indication on a display means 5 as to the state of the circuits being monitored. Each circuit 3 comprises a series of interconnected tiles 10 in a known location on the shuttle and is referred to as a protected grid series tile section.

Figure 3:
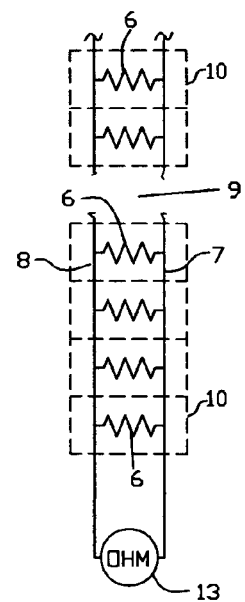
FIG. 3 is a schematic diagram indicating a loss in integrity in the tiles and circuit.

Specific operation of each protected grid series tile section will now be described with reference to FIG. 3. Parallel conductors 7 and 8 pass through, or are attached to, tiles 10 and are connected at their ends to a measurement device 13. In this case, measurement device 13 is an ohmmeter for measuring the resistance between the conductors 7 and 8. Measurement device 13 forms a part of the computing device 4. Between the conductors 7 and 8 at each tile 10 is a resistor 6 of known resistance. When there is no loss of integrity in the protected grid series tile section, the resistance measured at measurement device 13 is equal the known resistance of resistor 6 divided by the total number of resistors in that protected grid series. When there is a loss of integrity, such as a lost tile as indicated at 9, or a broken or loose tile, the circuit is broken and the resistance now measures the known resistance value divided by the number of remaining resistors on the same side of the break as the measuring device 13. When the measuring device 13, which is part of computing device 4, senses a rise in resistance value, computing device 4 sends a signal to display 5 indicating a loss of integrity in the protected grid series tile section. The magnitude of the new resistance value indicates the location of the break in the circuit. For example, if ten 1000 ohm resistors form a protected grid series tile section, then the baseline resistance would read 100 ohms (1000 ohms divided by 10 resistors) for that section. Should the 5th tile in the section be lost, there would only be 4 remaining tiles on the side of measuring device 13, and the new reading would be 250 ohms, indicating that the 5th tile was lost. By further measuring the resistance in the circuit at both ends of the protected grid series tile section, the extent of the damage can be assessed. Should the 5th and 6th tiles both be lost, the resistance at one end would read 250 ohms (1000 ohms divided by 4 remaining tiles), and the resistance at the other end would also now read 250 ohms (1000 ohms divided by these 4 remaining tiles), indicating that 2 tiles had been lost. The resistance of all protected grid series tile sections on the shuttle would be continually monitored by computing device 4 giving a real time indication of loss of integrity of any tiles.

Figure 4:
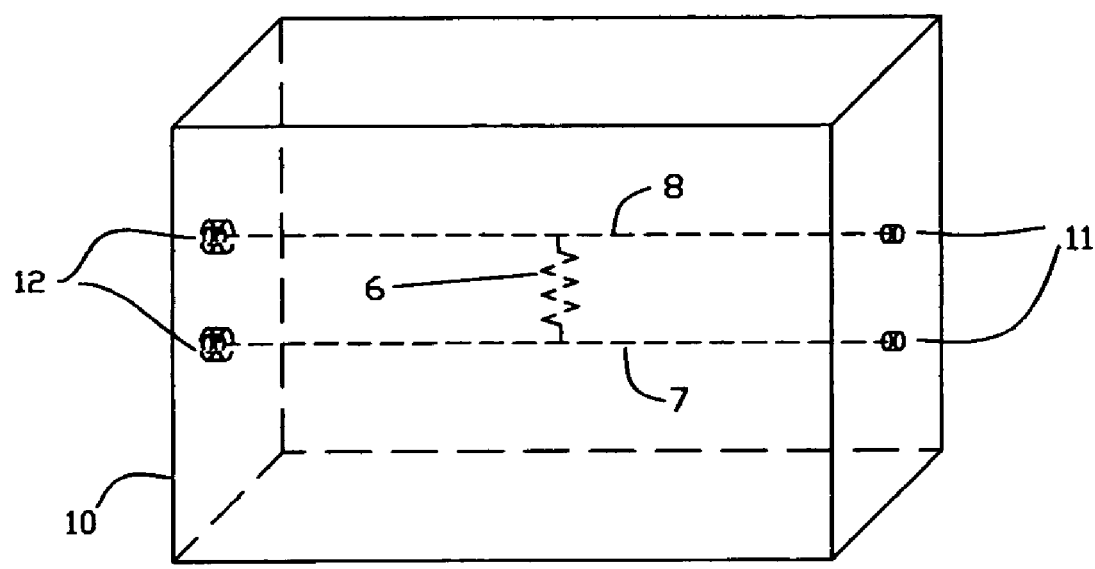
FIG. 4 shows one embodiment of a tile with the conductors embedded therein.

FIG. 4 shows one embodiment of a thermal protective tile incorporating the present invention. Tile 10 has parallel conductors 7 and 8, as well as resistor 6, formed within the body of the tile. The conductors 7 and 8, as well as resistor 6, can be embedded within the tile at the time of molding, or firing, of the silica tiles. The conductors and resistors may be made of a material that would withstand the heat of forming the tiles, as well as the heat generated during re-entry of the space vehicle. Connection means are provided at the ends of conductors 7 and 8 to electrically connect the tile 10 to the next adjacent tile in the protected grid series tile section. Connection means may be in the form of bayonet connectors with male portions 11 of the connectors formed at one end of the tile and female ends 12 formed at the other end. Alternatively, the connection means could be conductive lugs (not shown) that slightly protrude and contact corresponding lugs on the next tile.

Figure 5:
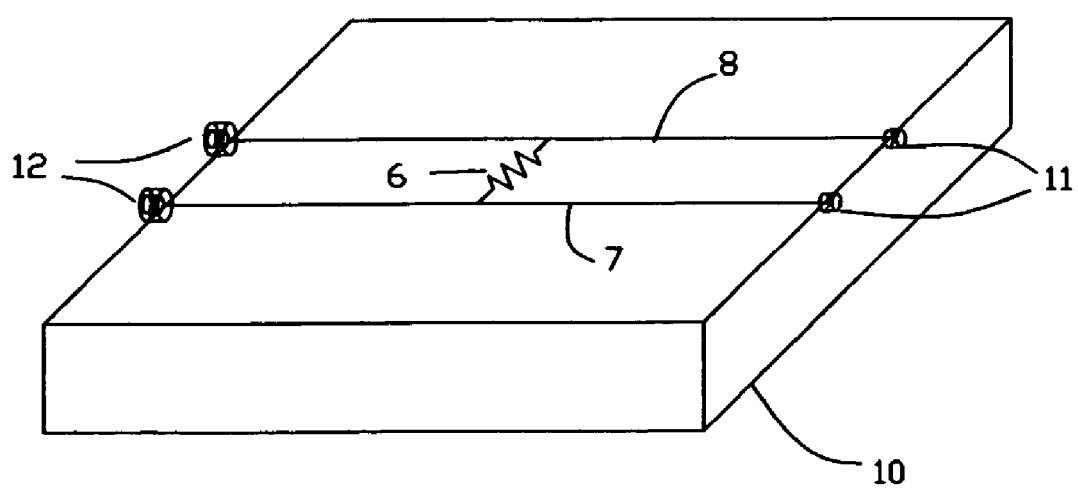
FIG. 5 shows a second embodiment with the conductors applied to the thermally protected side of a tile.

FIG. 5 shows a second embodiment where the conductors 7 and 8 and resistor 6 are applied directly to the thermally protected side of the tile 10 by means of an adhesive or other means, as is known. Connection means 11 and 12 are provided in a similar manner as that shown in FIG. 4.

In use, the present invention will provide an indication to the crew of the shuttle as to the integrity of the tiles, and upon loss of integrity, will provide an indication as to the severity of damage. If a loss of integrity occurs, steps can be taken to either repair the tiles before re-entry, or alternative action can be taken. Hopefully, with the aid of the present invention, further loss of life and shuttles due to loss of tile integrity can be avoided.

While the present invention has been specifically described with reference to particular embodiments, the invention should not be limited thereto, but should encompass any embodiments thereof which would be obvious to those in this art, as specifically set forth in the appended claims.

I claim:

1. A device for monitoring the integrity of a thermal protection tile system on a space craft, comprising:
   at least one pair of electrical conductors extending along, and in contact with, multiple tiles of the thermal protection tile system,
   multiple resistors of known resistance and known location extending between each one of said at least one pair of electrical conductors, each one of said multiple resistors in contact with one of said multiple tiles,
   resistance measuring means connected to each of two ends of said at least one pair of electrical conductors,
   computing means incorporating said resistance measuring means, and providing a real time output indicative of the integrity of said thermal protection tile system, and
   display means for providing a visual indication of the output of said computing means,
   wherein said computing means continually monitors the resistance in said at least one pair of electrical conductors in real time, alternately at each end of said two ends of said at least one pair of electrical conductors, and provides a visual indication at said display means of a significant resistance change, thereby providing an indication of both location and extent of loss of tile integrity of said thermal protection tile system.

2. The device for monitoring the integrity of the thermal protection tile system on a space craft of claim 1, wherein said at least one pair of electrical conductors is embedded within said tiles.

3. The device for monitoring the integrity of the thermal protection tile system on a space craft of claim 1, wherein said at least one pair of electrical conductors is adhered to a thermally protected side of the tile.

4. A method of monitoring the integrity of a thermal protection tile system on a spacecraft comprising the steps of:
   providing at least one pair of electrical conductors extending along, and in contact with, multiple tiles of the thermal protection tile system,
   providing multiple resistors of known resistance and known location extending between each one of said at least one pair of electrical conductors, each one of said multiple resistors in contact with one of said multiple tiles,
   providing resistance measuring means connected to two ends of said at least one pair of electrical conductors,
   providing computing means incorporating said resistance measuring means, said computing means providing an output indicative of the integrity of said thermal protection tile system, providing display means for providing a visual indication of the output of said computing means, continually measuring the resistance in said at least one pair of electrical conductors and comparing the measured resistance to a baseline resistance value, wherein a substantial difference between said measured resistance and said baseline resistance value is indicative of a loss of integrity in said thermal tile protection system, and, providing an output to said display means indicative of said loss of integrity in said thermal tile protection system.

5. The method of monitoring the integrity of the thermal protection tile system on a spacecraft of claim 4 further comprising:

determining the actual magnitude of the difference between said measured resistance and said baseline resistance value, providing an output to said display means indicative of the location of said loss of integrity, based on the determined actual magnitude of the difference between said measured resistance and said baseline resistance value.

6. The method of monitoring the integrity of the thermal protection tile system on a spacecraft of claim 4 further comprising:

continually measuring the resistance in said at least one pair of electrical conductors alternately at each of said two ends and comparing the measured resistance to a baseline resistance value, providing an output to said display means indicative of the location and extent of said loss of integrity, based on the determined actual magnitude of the difference between said measured resistance and said baseline resistance value at each of the two ends of said at least one pair of electrical conductors.

7. A device for monitoring the structural integrity of a structure, comprising:

at least one pair of electrical conductors extending along, and in contact with, said structure, multiple resistors of known resistance and known location extending between each one of said at least one pair of electrical conductors, each one of said multiple resistors in contact with said structure, resistance measuring means connected to each of two ends of said at least one pair of electrical conductors, computing means incorporating said resistance measuring means, and providing a real time output indicative of the integrity of said structure, and display means for providing a visual indication of the output of said computing means, wherein said computing means continually monitors the resistance in said at least one pair of electrical conductors in real time, alternately at each end of said two ends of said at least one pair of electrical conductors, and provides a visual indication at said display means of a significant resistance change, thereby providing an indication of both location and extent of loss of structural integrity of said structure.

* * * * *